(12) United States Patent
Kenzo et al.

(10) Patent No.: US 6,388,130 B2
(45) Date of Patent: May 14, 2002

(54) METHOD FOR PRODUCING AXIAL ASYMMETRIC COMPOUNDS, AND INTERMEDIATES FOR PRODUCING THE SAME

(75) Inventors: Sumi Kenzo, Hiratsuka; Noyori Ryoji, Aichi-ken; Ikariya Takao, Tokyo, all of (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 09/875,203

(22) Filed: Jun. 7, 2001

Related U.S. Application Data

(62) Division of application No. 09/471,247, filed on Dec. 23, 1999, now Pat. No. 6,323,353.

(30) Foreign Application Priority Data

Dec. 24, 1998 (JP) .............................................. 10-367755

(51) Int. Cl.$^7$ .............................. C07F 9/28; C07F 15/00; B01J 31/28; C07B 53/00
(52) U.S. Cl. .......................... 564/15; 556/21; 556/137; 502/162; 564/123; 564/180; 568/17
(58) Field of Search .......................... 564/15, 123, 180; 568/17; 556/21, 137; 502/162

(56) References Cited

FOREIGN PATENT DOCUMENTS

EP        1013658 A1  *  6/2000

OTHER PUBLICATIONS

Vyskocil et al., Tetrahedron Letters, vol. 39, No. 50, pp. 9289–9292 (Dec. 10, 1998).*
Tamio Hayashi et al., Tetrahedron: Asymmetry vol. 1 No. 3, pp. 151–154, 1990.
Toshimi Okada et al., Chemistry Letters pp. 999–1002, 1990.
Tamio Hayashi et al., J. Am. Chem. Soc. No. 104, pp. 180–186, 1982.
Stepan Vyskocil et al., J. Org. Chem. No. 63, pp. 7738–7748, 1998.
Hidemasa Takaya et al., J. Am. Chem. Soc. No. 109, pp. 1596–1597, 1987.
Yongkui Sun et al., Chem. Ind. (Dekker) No. 68, pp. 167–176, 1996.
Yasuhiro Uozumi et al., Tetrahedron vol. No. 15, pp. 4293–4302, 1994.
Yongkui Sun et al., J. Organometallic Chem. No. 548, pp. 65–72, 1997.

* cited by examiner

*Primary Examiner*—Porfirio Nazario-Gonzalez
(74) *Attorney, Agent, or Firm*—Birch, Stewart, Kolasch & Birch, LLP

(57) ABSTRACT

The invention provides a metal complex comprising a ligand and a metal. The ligand is an aminophosphine compound represented by the following formula (1)

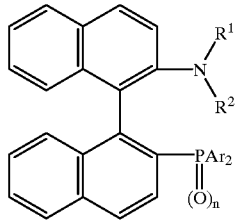

(1)

The metal is rhodium, ruthenium, iridium or nickel.

6 Claims, No Drawings

METHOD FOR PRODUCING AXIAL ASYMMETRIC COMPOUNDS, AND INTERMEDIATES FOR PRODUCING THE SAME

This application is a divisional of application Ser. No. 09/471,247, filed on Dec. 23, 1999, now U.S. Pat. No. 6,323,353, the entire contents of which are hereby incorporated by reference and for which priority is claimed under 35 U.S.C. §120; and this application claims priority of Application No. 367755/1998 filed in Japan on Dec. 24, 1998 under 35 U.S.C. §119.

BACKGROUND OF THE INVENTION

1. Industrial Applicable Field

The invention relates to a method for producing an axial asymmetric aminophosphine compound, an intermediate for producing the same, a method for producing a complex of a metal such as ruthenium, rhodium, iridium or nickel and the compound, and a catalyst for asymmetric hydrogenation or carbon-carbon bond formation using the complex.

2. Related Art Statement

There has been a number of reports describing complexes of transition metal elements available for asymmetric synthesis such as asymmetric hydrogenation, asymmetric isomerization or asymmetric hydrosilylation. Particularly, a complex of a transition metal element, such as ruthenium, rhodium, iridium, palladium or the like, with an optically active tertiary phosphine compound as its ligand has excellent properties as a catalyst for asymmetric synthesis.

Phosphine compounds with various chemical structures have been developed for further improving their performances as the catalysts ("Chemical Review" 32, "chemistry of organic metal complexes", page 237 to 238, edited by Japan Chemical Society, 1982) ("Asymmetric Catalysis in Organic Synthesis" Noyori Yoshiharu, A Wiley-Interscience Publication). 2,2'-Bis(diphenylphosphino)-1,1'-binaphthyl (referred to as "BINAP" below) is one of optically active phosphines having excellent properties. A complex of rhodium with "BINAP" is described in Japanese Patent Laid-Open publication "Kokai" 61973/1980 and a complex of ruthenium with "BINAP" is described in Japanese Patent Laid-Open publication "Kokai" 6390/1986. Further, a complex having 2,2'-bis[di(p-tolyl)phosphino]-1,1'-binapthyl (referred to as "p-Tol-BINAP" below) as its ligand is described in Japanese Patent Laid-Open publication "Kokai" 199898/1985 (rhodium) or 63690/1986 (ruthenium). These complexes are reported to provide good results for asymmetric hydrogenation and asymmetric isomerization. Further, Japanese Patent Laid-Open publication "Kokai" 255090/1991 discloses ruthenium complex of 2,2'-bis(di-3,5-dialkylphenyl)phosphino)-1,1'-binapthyl to have superior performance as a catalyst for asymmetric hydrogenation of, β-ketoesters. Further, palladium complexes of aminophosphine compounds have been used for asymmetric hydrosilylation. For example, a palladium complex having as its ligand an optically active aminophosphine compound with ferrocene bone structure is effective as a catalyst for asymmetric hydrosilylation of a conjugated diene compound with trichlorosilane (Tetrahedron Lett., Asymmetry, 1, 151(1990)). A palladium complex having an aminophosphine compound with N-sulfonyl group as its ligand is effective as a catalyst for hydrosilylation of styrene with chlorosilane (Chem. Lett. 999(1990)). Further, a nickel complex having as its ligand an aminophosphine compound having ferrocene bone structure is effective as a catalyst for asymmetric cross-coupling reaction of 1-phenylethylmagnesiuua chloride and vinyl chloride (J. Am. Chem. Soc. 104, 180(1982)). However, the above catalysts do not necessarily have sufficient chemical selectivity, enantioselectivity and catalytic activity depending on the reaction type or the substrate, leading to the needs for improving these kinds of catalysts.

Further, a phosphine compound 7 having a nitrogen atom in its molecule has been synthesized using an optically active 2-amino-2'-hydroxybinaphthyl as a starting material, according to the method described in a publication (J. Org. Chem. 63, 7738 (1988)). Moreover, an optically active 2-amino-2'-hydroxybinaphthyl has been obtained by the oxidative addition of 2-aminonaphthalene and 2-hydroxynaphthalene in the presence of sparteine or phenethylamine, or by the optical resolution of racemic mixture of 2-amino-2'-hydroxybinaphthyl. However, 2-aminonaphthalene is now difficult to obtain in the market due to its carcinogenicity and the above synthetic route using it is not desirable in the viewpoint of environmental protection.

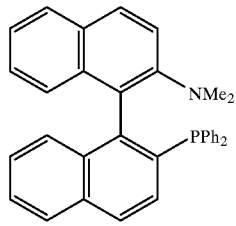

7

The inventive process utilizes safe 1,1'-bi-2-naphthol as the starting material for synthesizing a ligand composed of a phosphine having a nitrogen atom within its molecule, thus avoiding the above problems. Further, according to the examples in the above publication, as shown in the following scheme 1, the compound 8 is subjected to a substitution reaction of its allyl position with malonic ester in the presence of a catalyst containing palladium (so called "Tsuji reaction").

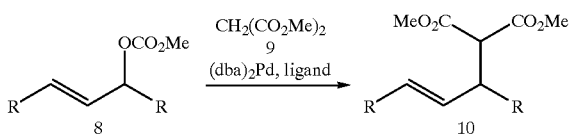

All the examples in the above publication is performed according to the above reaction scheme. Moreover, all the ligands used in the examples are selected from the following phosphine compounds 11, 12, 13 and 14, each having a dialkylamino group. The following free aminophosphine 15 is used only as a starting material and not used as a ligand throughout the examples.

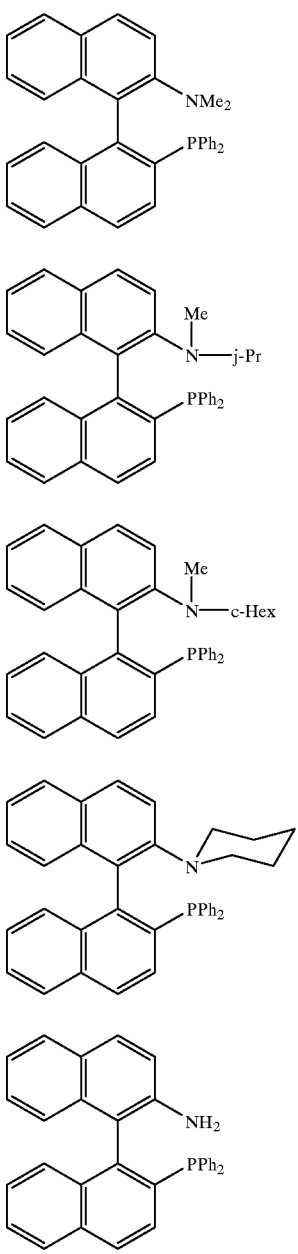

11

12

13

14

15

SUMMARY OF THE INVENTION

The object of the invention is to provide a metal complex which has a novel aminophosphine compound as its ligand and superior characteristics as a catalyst (chemical selectivity, enantioselectivity, catalytic activity) for asymmetric synthesis, especially asymmetric carbon-carbon bond formation and asymmetric hydrogenation.

The inventors have extensively studied many phosphine compounds to give a solution to the above problems and finally found that a complex containing a transition metal and an axially asymmetric and optically active aminophosphine compound having a nitrogen atom in its molecule, that is, 2-amino-2'-diarylphosphino-1-1'-binaphthyl (referred to as "MAP" below), is effective for asymmetric hydrogenation. The compound is an aminophosphine compound having binaphthyl group whose one naphthalene ring is connected to an amino group or a substituted amino group and the other naphthalene ring is connected to a diarylphosphino group. The inventors further found that the complex shows superior catalytic activity and enantioselectivity for asymmetric carbon-carbon bond formation.

The invention therefore provides a method for producing 2-amino-2'-diarylphosphino-1-1'-binaphthyl represented by the following formula (1-1)

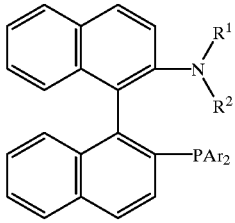
(1-1)

(referred to as "SMAP" below), or formula (1-2)

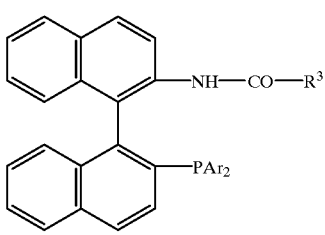
(1-2)

(referred to as "CMAP" below), or formula (1-3)

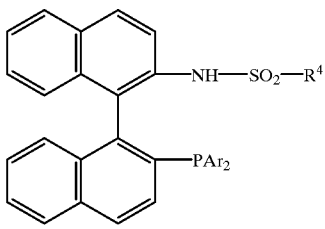
(1-3)

(referred to as "SUMAP" below). The invention further provides a complex of a transition metal having as its ligand one of the aminophosphine compounds represented by the following formulae (1-1), (1-2) and (1-3), and a method for producing the complex. Formula (1-1)

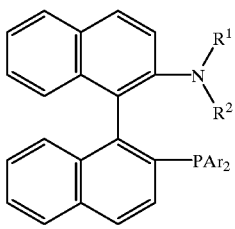
(1-1)

(In the formula, each Ar represents an aryl group (preferably phenyl group) which may be substituted with a halogen atom, a lower alkyl group having 1 to 4 carbon atom or an alkoxy group, with both Ar's being same or different with each other. $R^1$ and $R^2$ represent hydrogen atom, a cycloalkyl group having 5 to 7 carbon atoms, or an alkyl group having 1 to 6 carbon atom which may be substituted with a halogen atom, a lower alkoxy group or phenyl group, with $R^1$ and $R^1$ being same or different with each other.) The cycloalkyl group having 5 to 7 carbon atoms for $R^1$ and $R^2$ includes cyclopentyl group and cyclohexyl group. The alkyl group having 1 to 6 carbon atom which may be substituted with a halogen atom, a lower alkoxy group or phenyl group for $R^1$ and $R^2$ includes methyl, ethyl, butyl, hexyl, isopropyl, tert-butyl, fluoromethyl, 2,2,2-trifluoroethyl, 3,3,4,4,5,5,6,6,6-nonafluorohexyl, methoxymethyl, methoxyethoxymethyl, methoxypropyl, methoxybutyl, ethoxyethoxymethyl, methoxypropoxymethyl, butoxymethyl, benzyl, diphenylmethyl and phenylpropyl groups or the like, and may preferably be an alkyl group having 1 to 4 carbon atoms, methoxyethyl group or methoxyethoxymethyl group. Further, in the formula (1-1), Ar represents an aryl group (preferably phenyl group) which may be substituted with a halogen atom, a lower alkyl group having 1 to 4 carbon atom or an alkoxy group, and may preferably be unsubstituted phenyl group, p-tolyl group and 3,5-methylphenyl group.

Formula (1-2)

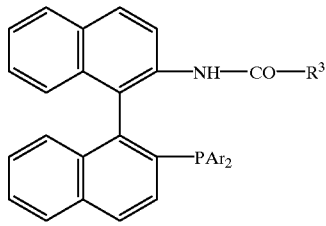

(1-2)

(In the formula, each Ar represents an aryl group (preferably phenyl group) which may be substituted with a halogen atom, a lower alkyl group having 1 to 4 carbon atom or an alkoxy group, with both Ar's being same or different with each other. $R^3$ represents a cycloalkyl group having 5 to 7 carbon atoms, or an alkyl group having 1 to 6 carbon atom which may be substituted with a halogen atom, a lower alkoxy group or phenyl group, substituted or unsubstituted phenyl group, or a lower alkoxy group.). The cycloalkyl group having 5 to 7 carbon atoms for $R^3$ includes cyclopentyl group, cyclohexyl group or the like. The alkyl group having 1 to 6 carbon atom which may be substituted with a hydrogen atom, a lower alkoxy group or phenyl group includes methyl, ethyl, butyl, hexyl, isopropyl, tert-butyl, fluoromethyl, 2,2,2-trifluoroethyl, 3,3,4,4,5,5,6,6,6-nonafluorohexyl, methoxymethyl, methoxyethoxymethyl, methoxypropyl, methoxybutyl, ethoxyethoxymethyl, methoxypropoxymethyl, butoxymethyl, benzyl, diphenylmethyl and phenylpropyl groups or the like, and may preferably be an alkyl group having 1 to 4 carbon atom or benzyl group. $R^3$ may be unsubstituted phenyl group or phenyl group substituted with a halogen atom, a lower alkyl group having 1 to 4 carbon atom or an alkoxy group, and may preferably be unsubstituted phenyl group, p-tolyl group or 3,5-dimethylphenyl group. The lower alkoxy group for $R^3$ includes methoxy, ethoxy, propoxy, butoxy, isopropoxy, tert-butoxy, benzyloxy groups or the like, and may preferably be methoxy group, tert-butoxy group and benzyloxy group. Further in the formula (1-2), Ar represents phenyl group which may be substituted with a halogen atom, a lower alkyl group having 1 to 4 carbon atom or an alkoxy group, and may preferably be unsubstituted phenyl group, p-tolyl group or 3,5-dimethylphenyl group.

Formula (1-3)

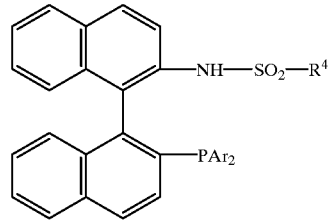

(1-3)

(In the formula, each Ar represents an aryl group (preferably phenyl group) which may be substituted with a halogen atom, a lower alkyl group having 1 to 4 carbon atom or an alkoxy group, with both Ar's being same or different with each other. $R^4$ represents a cycloalkyl group having 5 to 7 carbon atoms, or an alkyl group having 1 to 6 carbon atom which may be substituted with a hydrogen atom, a lower alkoxy group or phenyl group, or substituted or unsubstituted phenyl group.). The cycloalkyl group having 5 to 7 carbon atoms for $R^4$ includes cyclopentyl group, cyclohexyl group or the like. The alkyl group having 1 to 6 carbon atom, which may be substituted with a hydrogen atom, a lower alkoxy group or phenyl group, includes methyl, ethyl, butyl, hexyl, isopropyl, tert-butyl, fluoromethyl, 2,2,2-trifluoroethyl, 3,3,4,4,5,5,6,6,6-nonafluorohexyl, methoxymethyl, methoxyethoxymethyl, methoxypropyl, methoxybutyl, ethoxyethoxymethyl, methoxypropoxymethyl, butoxymethyl, benzyl, diphenylmethyl and phenylpropyl groups or the like, and may preferably be an alkyl group having 1 to 4 carbon atom. $R^4$ may be unsubstituted phenyl group or phenyl group substituted with a halogen atom, a lower alkyl group having 1 to 4 carbon atom or an alkoxy group, and may preferably be unsubstituted phenyl group, p-tolyl group or 3,5-dimethylphenyl group. Further in the formula (1-3), Ar represents an aryl group (preferably phenyl group) which may be substituted with a halogen atom, a lower alkyl group having 1 to 4 carbon atom and an alkoxy group, and may preferably be unsubstituted phenyl group, p-tolyl group or 3,5-dimethylphenyl group.

Aminophosphine compounds as important intermediates for synthesizing the inventive aminophosphine compounds (1-1). (1-2) and (1-3) are represented by the following formula (1-1-1)

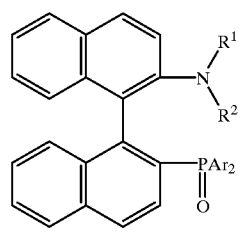

(1-1-1)

or the formula(1-2-1)

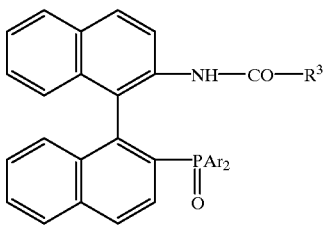
(1-2-1)

or the formula (1-3-1)

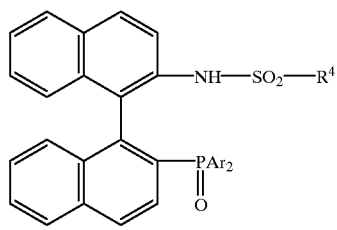
(1-3-1)

or the formula (5).

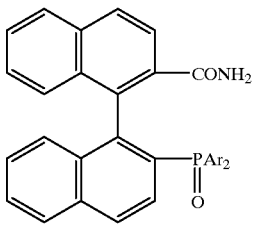
(5)

Formula (1-1-1)

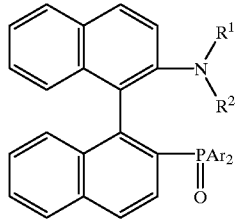
(1-1-1)

(In the formula, each Ar represents an aryl group (preferably phenyl group) which may be substituted with a halogen atom, a lower alkyl group having 1 to 4 carbon atom or an alkoxy group, with both Ar's being same or different with each other. $R^1$ and $R^2$ represent hydrogen atom, a cycloalkyl group having 5 to 7 carbon atoms, or an alkyl group having 1 to 6 carbon atom which may be substituted with a halogen atom, a lower alkoxy group or phenyl group, with $R^1$ and $R^2$ being same or different with each other.) The cycloalkyl group having 5 to 7 carbon atoms for $R^1$ and $R^2$ includes cyclopentyl group, cyclohexyl group or the like.

The alkyl group having 1 to 6 carbon atom for $R^1$ and $R^2$ which may be substituted with a halogen atom, a lower alkoxy group or phenyl group, includes methyl, ethyl, butyl, hexyl, isopropyl, tert-butyl, fluoromethyl, 2,2,2-trifluoroethyl, 3,3,4,4,5,5,6,6,6-nonafluorohexyl, methoxymethyl, methoxyethoxymethyl, methoxypropyl, methoxybutyl, ethoxyethoxymethyl, methoxypropoxymethyl, butoxymethyl, benzyl, diphenylmethyl and phenylpropyl groups or the like, and may preferably be an alkyl group having 1 to 4 carbon atom, methoxyethyl group and methoxyethoxymethyl group. Further, in the formula (1-1-1), Ar represents an aryl group (preferably phenyl group) which may be substituted with a halogen atom, a lower alkyl group having 1 to 4 carbon atom or an alkoxy group, and may preferably be unsubstituted phenyl group, p-tolyl group or 3,5-methylphenyl group.

Formula (1-2-1)

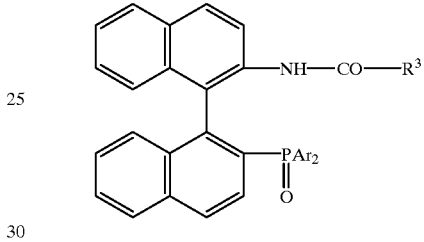
(1-2-1)

(In the formula, each Ar represents an aryl group (preferably phenyl group) which may be substituted with a halogen atom, a lower alkyl group having 1 to 4 carbon atom or an alkoxy group, with both Ar's being same or different with each other. $R^3$ represents a cycloalkyl group having 5 to 7 carbon atoms, or an alkyl group having 1 to 6 carbon atoms which may be substituted with a halogen atom, a lower alkoxy group or phenyl group, substituted or unsubstituted phenyl group, or a lower alkoxy group.). The cycloalkyl group having 5 to 7 carbon atoms for $R^3$ includes cyclopentyl group, cyclohexyl group or the like. The alkyl group having 1 to 6 carbon atom which may be substituted with a hydrogen atom, a lower alkoxy group or phenyl group includes methyl, ethyl, butyl, hexyl, isopropyl, tert-butyl, fluoromethyl, 2,2,2-trifluoroethyl, 3,3,4,4,5,5,6,6,6-nonafluorohexyl, methoxymethyl, methoxyethoxymethyl, methoxypropyl, methoxybutyl,, ethoxyethoxymethyl, methoxypropoxymethyl, butoxymethyl, benzyl, diphenylmethyl or phenylpropyl groups or the like, and may preferably be an alkyl group having 1 to 4 carbon atom or benzyl group. $R^3$ may be unsubstituted phenyl group or phenyl group substituted with a halogen atom, a lower alkyl group having 1 to 4 carbon atom or an alkoxy group, may preferably be unsubstituted phenyl group, p-tolyl group or 3,5-dimethylphenyl group. The lower alkoxy group for $R^3$ includes methoxy, ethoxy, propoxy, butoxy, isopropoxy, tert-butoxy, benzyloxy groups or the like, and may preferably be methoxy group, tert-butoxy group or benzyloxy group. Further in the formula (1-2-1), Ar represents an aryl group (preferably phenyl group) which may be substituted with a halogen atom, a lower alkyl group having 1 to 4 carbon atom or an alkoxy group, and may preferably be unsubstituted phenyl group, p-tolyl group or 3,5-dimethylphenyl group.

Formula (1-3-1)

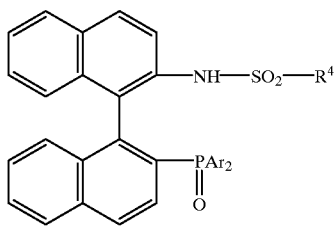

(1-3-1)

(In the formula, each Ar represents an aryl group (preferably phenyl group) which may be substituted with a halogen atom, a lower alkyl group having 1 to 4 carbon atom or an alkoxy group, with both Ar's being same or different with each other. $R^4$ represents a cycloalkyl group having 5 to 7 carbon atoms, or an alkyl group having 1 to 6 carbon atom which may be substituted with a hydrogen atom, a lower alkoxy group or phenyl group, or substituted or unsubstituted phenyl group.). The cycloalkyl group having 5 to 7 carbon atoms for $R^4$ includes cyclopentyl group, cyclohexyl group or the like. The alkyl group having 1 to 6 carbon atoms, which may be substituted with a hydrogen atom, a lower alkoxy group or phenyl group, includes methyl, ethyl, butyl, hexyl, isopropyl, tert-butyl, fluoromethyl, 2,2,2-trifluoroethyl, 3,3,4,4,5,5,6,6,6-nonafluorohexyl, methoxymethyl, methoxyethoxymethyl, methoxypropyl, methoxybutyl, ethoxyethoxymethyl, methoxypropoxymethyl, butoxymethyl, benzyl, diphenylmethyl and phenylpropyl groups or the like, and may preferably be an alkyl group having 1 to 4 carbon atom. $R^4$ may be unsubstituted phenyl group or phenyl group substituted with a halogen atom, a lower alkyl group having 1 to 4 carbon atom or an alkoxy group, and may preferably be unsubstituted phenyl group, p-tolyl group or 3,5-dimethylphenyl group. Further in the formula (1-3-1), Ar represents an aryl group (preferably phenyl group) which may be substituted with a halogen atom, a lower alkyl group having 1 to 4 carbon atom or an alkoxy group, and may preferably be unsubstituted phenyl group, p-tolyl group or 3,5-dimethylphenyl group.

Formula (5)

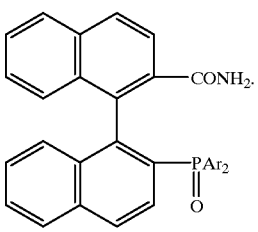

(5)

(In the formula, each Ar represents an aryl group (preferably phenyl group) which may be substituted with a halogen atom, a lower alkyl group having 1 to 4 carbon atom or an alkoxy group, with both Ar's being same or different with each other.). Ar represents phenyl group which may be substituted with a halogen atom, a lower alkyl group having 1 to 4 carbon atom or an alkoxy group, and may preferably be unsubstituted phenyl group, p-tolyl group or 3,5-dimethylphenyl group.

The inventive 2-amino-2'-diarylphosphino-1-1'-binaphthyl (1-1), (1-2) or (1-3), 2-amino-2'-diarylphosphinyl-1,1'-binaphthyl(1-1-1), (1-2-1) or (1-3-1), or 2-carbamoyl-2!-diarylphosphinyl-1-1'-binapthyl (5) includes their optically active isomers, that is, (+) and (−) isomers. The invention includes the (+) isomer, (−) isomer, and the racemic mixture of each compound.

Although the invention will be described below further in detail mainly in reference to a compound (−)-SMAP represented by the following formula (1-1a ) as a particular example for simplicity, the invention is not limited to the particular example.

Formula (1-1a)

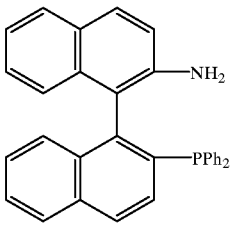

(1-1a)

The aminophosphine compound (1-1a) is an example of the inventive compound (1-1) wherein both Ar's are phenyl groups and $R^1$ and $R^2$ are both hydrogen atoms. The compound (1-1a) may be synthesized by the following scheme 2. That is, alkaline hydrogen peroxide is reacted with known (+)-cyanophosphine oxide (4a) (Tetrahedron 50, 4293 (1994)) in DMSO to provide carbamoyl phosphine oxide (5a), which is then reacted with sodium methoxide and bromine in a mixture of methanol and dioxane to provide a methoxycarbonyl compound (1-2b-1). Carbamoyl phosphine oxide (5a) may be reacted with a metal alkoxide and bromine in an organic solvent to provide an alkoxycarbonylaminophosphine oxide compound being represented by the formula (1-2-1), in which each Ar is phenyl group which may be substituted with a halogen atom, a lower alkyl group or an alkoxy group with Ar's being same or different with each other and $R^3$ is a lower alkoxide group. The above metal alkoxide may be sodium methoxide, potassium methoxide, lithium methoxide, sodium ethoxide, potassium ethoxide, lithium ethoxide, sodium benzyloxide, sodium tert-butoxide, potassium tert-butoxide or the like.

The compound (1-2b-1) is then hydrolyzed by effecting a strong alkali in a solvent containing water, preferably by effecting potassium hydroxide in methanol containing water, to provide an aminophosphine oxide (1-1a-1). The compound (1-1a-1) may be reduced by trichlorosilane to provide a compound of the formula (1-1a), that is, (−)-SMAP), in which Ar is phenyl group and $R^1$ and $R^2$ are hydrogen atoms in the formula (1-1) with a high yield. (+)-SMAP may be produced by applying the similar scheme using (−)-cyanophosphine oxide.

When using racemic mixture of (+)-cyanophosphine oxide and (−)-cyanophosphine oxide as the starting material for producing the inventive compound (1-1a), its racemic mixture will be obtained. Therefore, the racemic mixture or only one of its optically active bodies may be produced according to the object of the resultant compound.

(Scheme 2)

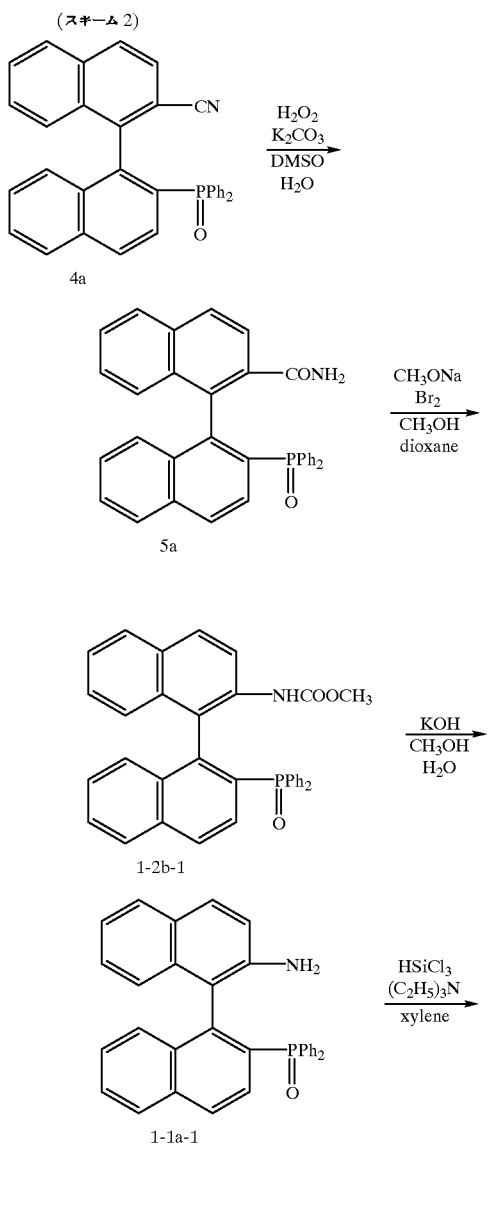

One of the inventive compound (1-1) with $R^1$ being methyl group and $R^2$ being hydrogen atom, that is, the compound (1-1b), may be produced by treating the compound (1-2b-1) with a reducing agent, such as borane, according to the following scheme.

(Scheme 3)

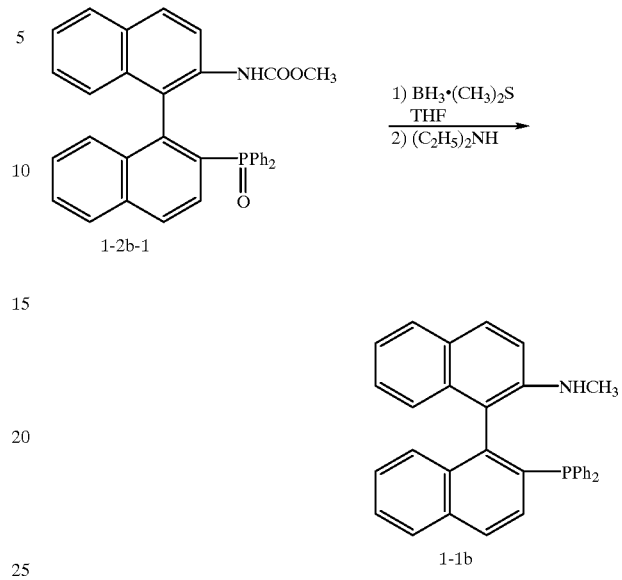

The inventive compounds (1-1) with $R^1$ being ethyl group and $R^2$ being hydrogen atom (compound (1-1c)) and with $R^1$ being benzyl group and $R^2$ being hydrogen atom (compound (1-1d)) may be produced by treating the compound (1-1a) with the corresponding acid chlorides, acetyl chloride or benzoyl chloride followed by the treatment with a reducing agent such as borane etc.

An acid chloride may be used for producing a compound represented by the formula (1-1) wherein $R^1$ is a cycloalkyl group having 5 to 7 carbon atoms or an alkyl group which may be substituted with a halogen atom, a lower alkoxy group or phenyl group and $R^2$ is hydrogen atom. Such acid chloride includes acetyl chloride, propionyl chloride, butyryl chloride, isobutyryl chloride, cyclohexanecarbonyl chloride, benzoyl chloride, acetyl bromide or the like.

(Scheme 4)

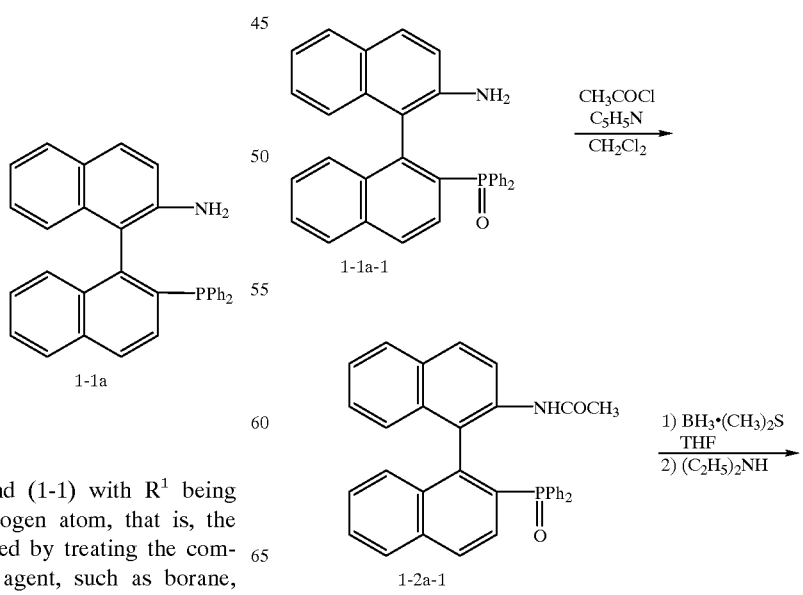

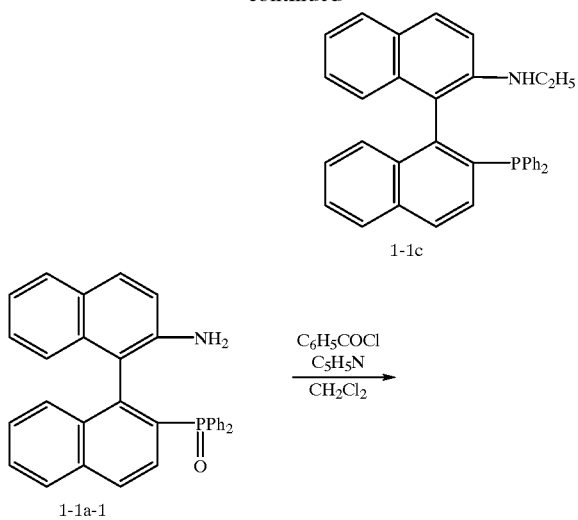

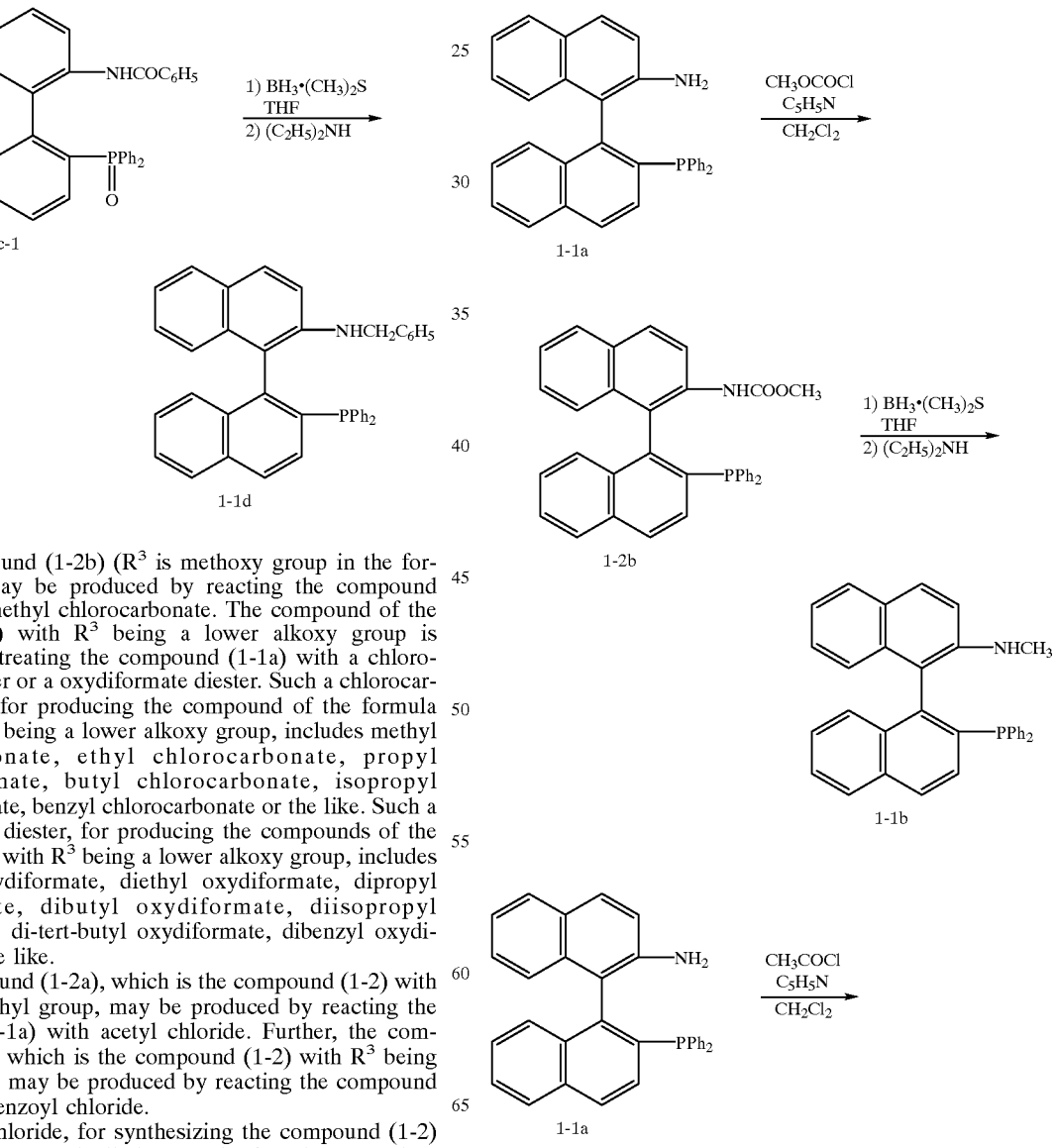

atoms, includes cyclopentylcarbonyl chloride, cyclohexylcarbonyl chloride or the like. The acid chloride, for producing the compound (1-2) with $R^3$ being an alkyl group which may be substituted with a halogen atom, a lower alkoxy group or phenyl group, includes acetyl chloride, propionyl chloride, burylyl chloride, valeryl chloride, hexanoyl chloride, heptanoyl chloride, isobutyryl chloride, pyvaloyl chloride, fluoroacetyl chloride, 2,2,2-trifluoroacetyl chloride, 3,3,4,4,5,5,6,6,6-nonafluoroheptanoyl chloride, methoxyacetyl chloride, methoxyethoxyacetyl chloride, methoxybutyroyl chloride, methoxypentanoyl chloride, ethoxyethoxyacetyl chloride, methoxypropoxyacetyl chloride, butoxyacetyl chloride, benzoyl chloride, diphenyacetyl chloride, phenylbutyroyl chloride or the like, and may preferably be acetyl chloride, propionyl chloride, butyryl chloride, valeryl chloride or benzoyl chloride. The compounds (1-1b), (1-1c) and (1-1d) may be prepared by treating the corresponding compounds (1-2b), (1-2a) and (1-2c) with a reducing agent such as borane or the like.

The compound (1-2b) ($R^3$ is methoxy group in the formula (1-2))may be produced by reacting the compound (1-1a) with methyl chlorocarbonate. The compound of the formula (1-2) with $R^3$ being a lower alkoxy group is produced by treating the compound (1-1a) with a chlorocarbonate ester or a oxydiformate diester. Such a chlorocarbonate ester, for producing the compound of the formula (1-2) with $R^3$ being a lower alkoxy group, includes methyl chlorocarbonate, ethyl chlorocarbonate, propyl chlorocarbonate, butyl chlorocarbonate, isopropyl chlorocarbonate, benzyl chlorocarbonate or the like. Such a oxydiformate diester, for producing the compounds of the formula (1-2) with $R^3$ being a lower alkoxy group, includes dimethyl oxydiformate, diethyl oxydiformate, dipropyl oxydiformate, dibutyl oxydiformate, diisopropyl oxydiformate, di-tert-butyl oxydiformate, dibenzyl oxydiformate or the like.

The compound (1-2a), which is the compound (1-2) with $R^3$ being methyl group, may be produced by reacting the compound (1-1a) with acetyl chloride. Further, the compound (1-2c), which is the compound (1-2) with $R^3$ being phenyl group, may be produced by reacting the compound (1-1a) with benzoyl chloride.

The acid chloride, for synthesizing the compound (1-2) with $R^3$ being a cycloalkyl group having 5 to 7 carbon

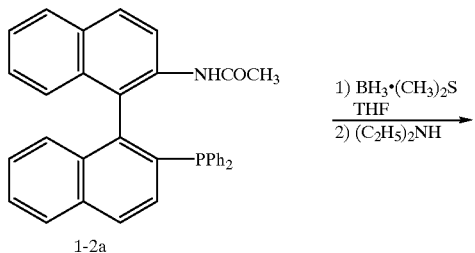

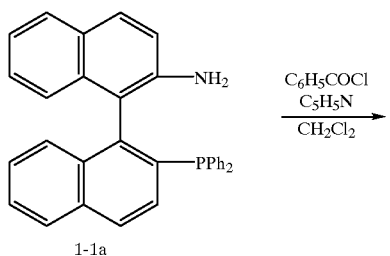

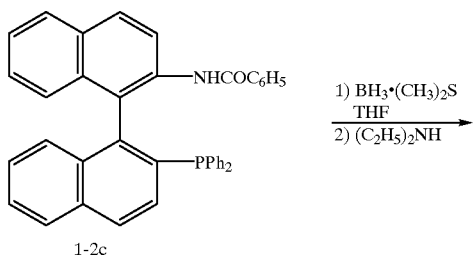

The compound (1-3a), which is the compound (1-3) with R⁴ being methyl group, may be prepared by treating the compound (1-1a-1) with methanesulfonyl chloride to provide the compound (1-3a-1), followed by the treatment with a reducing agent such as trichlorosilane or the like.

Further, the compound (1-3a) may be prepared by reacting the compound (1-1a) with methanesulfonyl chloride.

An organic sulfonyl chloride, used for producing the compound(1-3) with R⁴ being a cycloalkyl group having 5 to 7 carbon atoms, includes cyclopentanesulfonyl chloride, cyclohexanesulfonyl chloride or the like. An organic sulfonyl chloride, used for producing the compound(1-3) with R⁴ being an alkyl group having 1 to 6 carbon atom which may be substituted with a halogen atom, a lower alkoxy group or phenyl group, includes methanesulfonyl chloride, ethanesulfonyl chloride, butanesulfonyl chloride, hexanesulfonyl chloride, isopropylsulfonyl chloride, tert-butyl sulfonyl chloride, fluoromethanesulfonyl chloride, 2,2,2-trifluoroethanesulfonyl chloride, 3,3,4,4,5,5,6,6,6-nonafluorohexylsulfonyl chloride, methoxymethylsulfonyl chloride, methoxyethoxymethylsulfonyl chloride, methoxypropylsulfonyl chloride, methoxybutylsulfonyl chloride, ethoxyethoxymethylsulfonyl chloride, methoxypropoxymethylsulfonyl chloride, butoxymethylsulfonyl chloride, benzylsulfonyl chloride, diphenylmethylsulfonyl chloride, phenylpropylsulfonyl chloride or the like. An organic sulfonyl chloride, used for preparing the compound (1-3) with R⁴ being substituted or unsubstituted phenyl group, includes benzenesulfonyl chloride, p-toluenesulfonyl chloride or the like. The organic sulfonyl chloride may preferably be methanesulfonyl chloride or benzenesulfonyl chloride.

(Scheme 6)

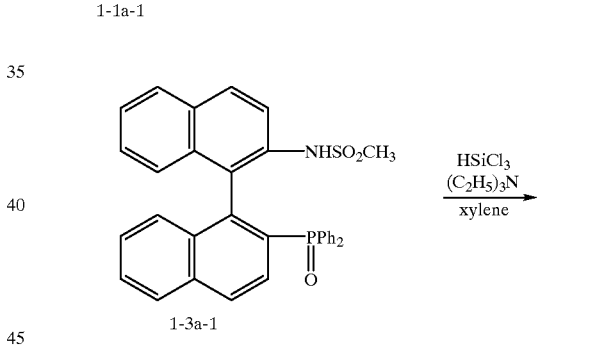

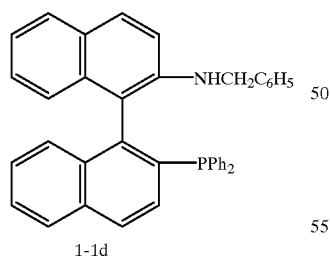

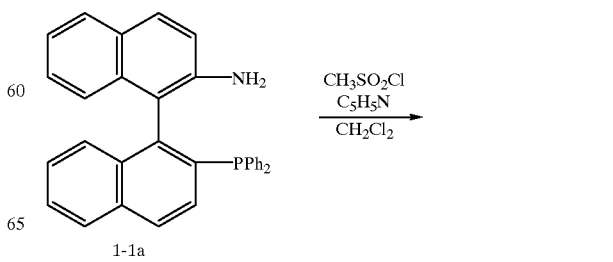

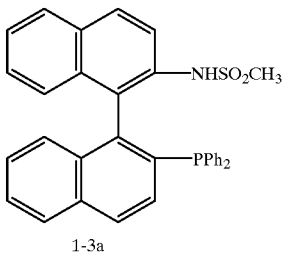

1-3a

The 2-amino-2'-diarylphosphino-1-1'-binaphthyl (1) of the invention forms a complex as its ligand with a transition metal. Such transition metal includes rhodium, ruthenium, iridium, nickel or the like. The complexes of the transition metals may be produced according to the known methods.

For example, the complex of rhodium may be synthesized by reacting the inventive 2-amino-2'-diarylphosphino-1-1'-binaphthyl (1) with bis(cycloocta-1,5-diene)rhodium (I) tetrafluoroborate, according to the method described in "reviews on experimental chemistry: fourth edition "volume 18 "organic metal complex" pages 339 to 344 (edited by Japan Chemical society, published in 1991 by Maruzen). Such rhodium complexes include, for example, the followings.

Rh(L)Cl, Rh(L)Br, Rh(L)I,
[Rh(cod)(L)]BF$_4$, [Rh(cod)(L)]ClO$_4$,
[Rh(cod)(L)]PF$_6$, [Rh(cod)(L)]BPh$_4$,
[Rh(nbd)(L)]BF$_4$, [Rh(nbd)(L)]ClO$_4$,
[Rh(nbd)(L)]PF$_6$, [Rh(nbd)(L)]BPh$_4$
("cod" means 1,5-cyclooctadiene and "nbd" means norbornadiene)

The complex of ruthenium may be synthesized by heating and refluxing [Ru(cod)Cl$_2$]n with MAP in the presence of triethylamine in toluene to react them with each other, according to the method described in a publication (J. Chem. Soc. Chem. Commun. 922 (1988)), or by heating and stirring [Ru(p-cymene)I$_2$]$_2$ with MAP in dichloromethane and ethanol, according to the method described in a publication (J. Chem. Soc. Chem. Commun. 1208 (1989)). Such ruthenium complexes include, for example, the followings.

Ru(OAc)$_2$(L), Ru$_2$Cl$_4$(L)$_2$NEt$_3$,
[RuCl(benzene)(L)]Cl, [RuBr(benzene)(L)]Br, [RuI(benzene)(L)]I,
[RuCl(p-cymene)(L)]Cl, [RuBr(p-cymene)(L)]Br, [RuI(p-cymene)(L)]I,
[Ru(L)](BF$_4$)$_2$, [Ru(L)](ClO$_4$)$_2$, [Ru(L)](PF$_6$)$_2$, [Ru(L)](BPF$_4$)$_2$ The complex of iridium may be prepared by reacting MAP with [Ir(cod)$_2$']BF$_4$ in tetrahydrofuran with stirring, according to the method described in a publication (J. Chem. Soc. Chem. Commun. 1553 (1970)). Such iridium complexes include the followings.

Ir(L)Cl, Ir(L)Br, Ir(L)I,
[Ir(cod)(L)]BF$_4$, [Ir(cod)(L)]ClO$_4$,
[Ir(cod)(L)]PF$_6$, [Ir(cod)(L)]BPh$_4$,
[Ir(nbd)(L)]BF$_4$, [Ir(nbd)(L)]ClO$_4$,
[Ir(nbd)(L)]PF$_6$, [Ir(nbd)(L)]BPh$_4$ The complex of nickel may be prepared according to the method described in "reviews on experimental chemistry: fourth edition "volume 18 "organic metal complex" page 376 (edited by Japan Chemical society, published in 1991 by Maruzen).

The complex of nickel may be prepared by dissolving MAP and nickel chloride in mixed solvent of isopropanol and methanol and heating the mixture with stirring, according to the method described in a publication (J. Am. Chem. Soc. 113, 9887, (1991)). Such nickel complexes include the followings.

NiCl$_2$(L), NiBr$_2$(L), NiI$_2$(L)

The complexes of transition metals, having the opticallyl active aminophosphine compound MAP as the ligand, is useful as a catalyst for asymmetric hydrogenation. The complex may be used as a catalyst after or without purifying it.

Among the above complexes of transition metals, the complex containing iridium and the optically active aminophosphine compound SMAP as the ligand provides enantioselectivity higher than that of a complex of ruthenium containing BINAP, p-Tol-BINAP or the like as its ligand, when catalyzing asymmetric hydrogenation of geraniol.

(Scheme 7)

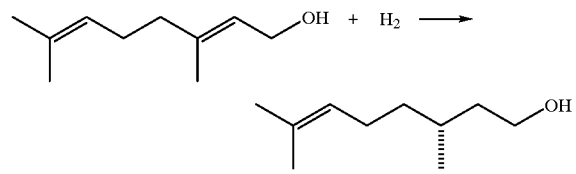

The asymmetric hydrogenation of geraniol, nerol and γ-geraniol using a ruthenium complex has already been reported (J. Am. Chem. Soc. 109, 1596, 4129 (1987); J. Organomet. Chem. 548, 65 (1997); Chem. Ind. (Dekker), 68, (1996)). When geraniol, nerol and γ-geraniol are subjected to asymmetric hydrogenation using the rhutenium complex of (S)-BINAP to produce citronellol, one of the enantiomers of citronellol is obtained when geraniol is hydrogenated and the other is obtained when nerol or γ-geraniol is hydrogenated.

(Scheme 8)

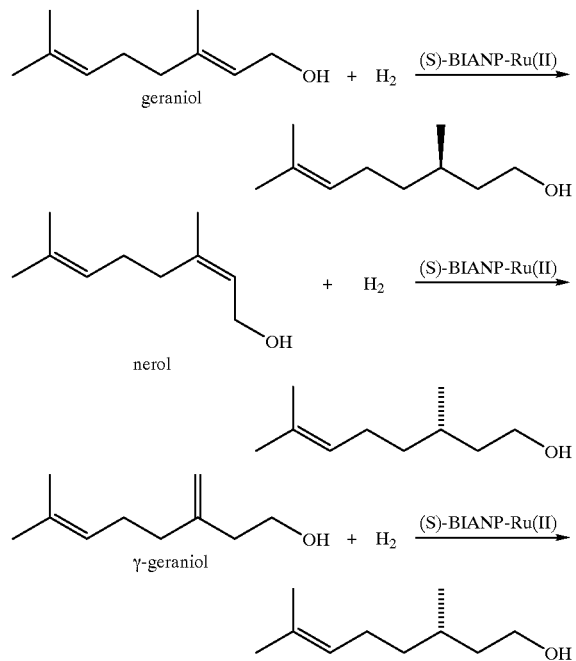

On the contrary, the asymmetric hydrogenation of either of geraniol, nerol or γ-geraniol using the iridium complex according to the invention provides only one of the enantiomers of citronellol, as shown in the following scheme 9. Therefore, even if the starting material of the asymmetric hydrogenation is a mixture of the trans-and cis-bodies of an allyl alcohol such as geraniol and nerol, the resulting product such as citronellol is composed of only one of its enantiomers. On the contrary, the above prior art using the ruthenium complex of (S)-BINAP inevitably produces a mixture of the enantiomers, when the starting material of the asymmetric hydrogenation is a mixture of geraniol and nerol.

(Scheme 9)

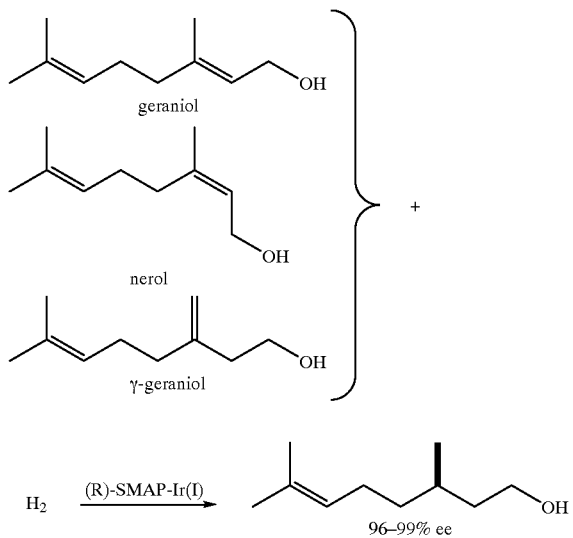

The inventive complex containing the 2-methylsulfonylamino-2'-diarylphosphino-1,1'-binaphthyl (SUMAP) as its ligand provides a high enantioselectivity in asymmetric carbon-carbon bond formation between norbornene and phenyl trifluoromethanesulfonate under the pressure of hydrogen.

(Scheme 10)

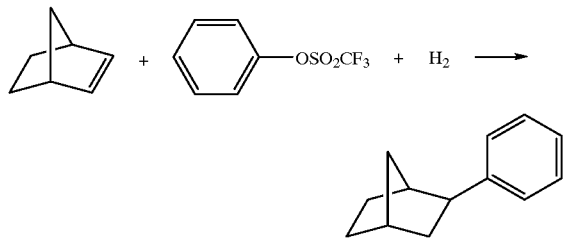

The inventive MAP may be used as a ligand of a complex of a transition metal. Such complex of a transition metal containing SMAP as its ligand is useful as a catalyst for asymmetric hydrogenation. In particular, its iridium complex provides enantioselectivity, as a catalyst for asymmetric hydrogenation of an allyl alcohol, higher than that of ruthenium complex containing BINAP or p-TolBINAP, and thus very useful in an industry. Further, the complex of 2-methylsulfonylamino-2'-diphenylphopsphino-1-1'-binaphthyl(SUMAP) provides a high enantioselectivity in asymmetric carbon-carbon bond formation between norbornene and phenyl trifluoromethanesulfonate. It is also possible to provide a compound with a desired absolute configuration in asymmetric sysnthesis, by using a complex of a transition metal having only one of (−)-and (+)-bodies of the inventive ligand as a catalyst for the asymmetric synthesis.

EXAMPLES

The invention will be described in detail referring to the specific examples, which do not particularly limit the scope of the invention.

The following apparatuses were used for measuring properties in the following examples.

| nuclear magnetic resonance | "$^1$H-NMR Bruker DRX500" (500 MHz) "$^{31}$P-NMR Bruker DRX500" (202 MHz) |
|---|---|
| melting point | "Yanaco MP-500D" |
| angle of rotation | "DIP-4" Nihon Bunko |
| infrared ray spectroscopy | "Nicolet Avatar 360" |

Example 1

Synthesis of (+)-2-carbamoyl-2'-diphenylphosphinyl-1,1'-binaphthyl: the formula (5a)

9.99 g (20.8 mmol) of (+)-2-cyano-2'-diphenylphosphinyl -1,1'-binaphthyl (the formula (4a)), synthesized according to the known method (Tetrahedron 50, 4293, (1994)), was weighed and added into a four neck flask, which was equipped with a thermometer, a cooling tube and a dropping funnel with an equalizer. 100 ml of Dimethylsulfoxide was added into the flask. 50 ml of 30 percent aqueous solution of hydrogen peroxide was added at 0° C. followed by the addition of potassium carbonate (57.6 g) and sonication for 25 minutes. Thereafter, 43 ml of water was added and 43 ml of dimethylsulfoxide was then added, followed by sonication to the resultant mixture for 30 minutes, which was then stirred for 15 hours. The resultant mixture was extracted with 300 ml of ethyl acetate, and the extract was washed with 100 ml of saturated aqueous solution of ammonium chloride and 200 ml of brine, and then dried over anhydrous sodium sulfate. The solvent was evaporated under a reduced pressure and the residue was purified using a silica gel column chromatography (eluent: ethyl acetate) to obtain 10.2 gram of the titled compound.

mp: 121.7° C.
$^1$H-NMR (CDCl$_3$) δ: 9.44 (bs, 1H), 7.91(d, J=8.3 Hz, 1H), 7.86(d, J=8.8 Hz, 2H), 7.8–7.7(m, 3H), 7.62(d, J=7.8 Hz, 1H), 7.6–7.4(m, 5H), 7.3–7.2(m, 1H), 7.2–7.0(m, 5H), 7.0–6.9(m, 2H), 6.64(t, J=7.0 Hz, 1H), 6.33(d, J=8.3 Hz, 1H), 5.52(bs, 1H)
$^{31}$P-NMR (CDCl$_3$): δ: 30.9
[α]D (CHCl$_3$, c=1, 24° C.): 157°
IR(CHCl$_3$) cm$^{-1}$: 1662, 1119

Example 2

Synthesis of (−)-2-methoxycarbonylamino-2'-diphenylphosphinyl-1,1'-binaphthyl: the Formula (1-2b-1)

161 ml of methanol was added to 19.9 ml of 28 percent sodium methoxide (97.3 mmol) under the flow of nitrogen, 1.84 ml (35.7 mmol) of bromine was added dropwise at −78° C. and the resultant mixture was stirred for 15 minutes. To this mixture, solution of 8.07 gram (16.2 mmol) of (+)-2-carbamoyl-2'-diphenylphosphinyl-1,1'-binaphthyl (the formula (5a)) dissolved in mixture of methanol (145 ml) and dioxane (145 ml) was added dropwise over 1 hour. The temperature of the mixture was elevated to room temperature and then stirred for 1 hour at 55° C. The reaction mixture was cooled to room temperature, extracted with 200 ml of ethyl acetate, washed with 100 ml of saturated aqueous solution of ammonium chloride and 100 ml of brine, and then dried over anhydrous sodium sulfate. The solvent was evaporated under a reduced pressure and the residue was purified using a silica gel column chromatography (eluent: 2:1 mixture of ethyl acetate and hexane) to obtain 8205 gram of the titled compound.

mp: 127.8° C.
$^1$H-NMR (CDCl$_3$) δ: 8.72 (bs, 1H), 7.9–7.6(m, 5H), 7.65(d, J=8.8 Hz, 1H), 7.6–7.4(m, 6H), 7.3–7.1(m, 4H), 7.08(d, J=8.8 Hz, 1H), 6.94 (t, J=7.1 Hz, 1H), 6.80(t, J=7.0 Hz, 1H), 6.7–6.6(m, 2H), 6.50(d, J=6.8 Hz, 1H), 3.04(bs, 3H)
$^{31}$P-NMR (CDCl$_3$): δ: 28.2
[α]D (CHCl$_3$, c=1, 24° C.): −155°
IR(CHCl$_3$) cm$^{-1}$: 1723, 1507, 1238, 1171, 1115

Example 3
Synthesis of (−)-2-amino-2'-diphenylphosphinyl-1,1'-binaphthyl: the Formula (1-1a-1)
8.01 gram (15.2 mmol) of (−)-2-methoxycarbonylamino-2'-diphenylphosphinyl-1,1'-binaphthyl (the formula (1-2b-1)) was dissolved in 304 ml of methanol. To the solution, 152 ml of 40 percent aqueous solution of potassium hydroxide was added dropwise over 30 minutes and then stirred at 95° C. for 2 hours. The resultant mixture was extracted with 300 ml of ethyl acetate, and the extract was washed with brine, and then dried over anhydrous sodium sulfate. The solvent was evaporated under a reduced pressure and the residue was purified using a silica gel column chromatography (eluent: ethyl acetate) to obtain 7.16 gram of the titled compound.

mp: 133.3° C.
$^1$H-NMR (CDCl$_3$) δ: 8.0–7.8(m, 2H), 7.8–7.6(m, 5H), 7.6–7.4(m, 1H), 7.4–7.3(m, 5H), 7.3–7.1(m, 4H), 7.1–6.9 (m, 1H), 6.9–6.8(m, 3H), 6.8–6.7(m, 2H), 6.51(d, J=8.3 Hz, 1H), 3.94(bs, 2H)
$^{31}$P-NMR (CDCl3): δ: 27.1
[α]D (CHCl$_3$, c=1, 24° C.): −199°
IR (CHCl$_3$) cm$^{-1}$: 1662, 1172, 1115

Example 4
Preparation of [Ir(cod)((−)-SMAP)]BF$_4$
4.5 mg (0.01 mmol) of [Ir(cod)$_2$]BF$_4$, 5.0 mg (0.01 mmol) of (−)-SMAP: the formula (1-1a) and 1 ml of chloroform were mixed and stirred for 30 minutes at room temperature in a shrenck tube with a volume of 20 ml. The solvent was evaporated under a reduced pressure and the residue was dried under vacuum to obtain 9.5 mg of the titled compound.
$^{31}$P-NMR (CDCl$_3$): δ: 16.3

Example 5
Synthesis of (−)-2-methylamino-2'-diphenylphosphino-1,1'-binaphthyl: the Formula (1-1b)
3.59 gram (6.81 mmol) of (−)-2-methoxycarbonylamino-2-diphenylphosphinyl-1,1'-binaphthyl (the formula (1-2b-1)) was dissolved in 170 ml of tetrahydrofuran, under the flow of nitrogen. To the solution, 27.2 ml of tetrahydrofuran solution (2M) of borane-dimethyl sulfide complex was added at 0° C. over 30 minutes and the resultant mixture was stirred for 18 hours at 88° C. The resultant reaction solution was extracted with 300 ml of ethyl acetate, and the extract was washed with 100 ml of saturated aqueous solution of ammonium chloride and 100 ml of brine, and then dried over anhydrous sodium sulfate. The solvent was evaporated under a reduced pressure. To the residue, 272 ml of diethylamine was added and stirred at room temperature for 30 minutes. After evaporating diethylamine, the residue was purified using a silica gel column chromatography (eluent: 1:16 mixture of ethyl acetate and hexane) to obtain 3.05 gram of the titled compound.

mp: 100.2° C.
$^1$H-NMR (CDCl$_3$) δ: 7.9–7.8(m, 3H), 7.73(d, J=8.3 Hz, 1H), 7.5–7.4(m, 2H), 7.3–6.9(m, 15H), 6.70(d, J=8.3 Hz, 1H), 3.04(bs, 1H), 2.37(s, 3H)
$^{31}$P-NMR (CDCl$_3$): δ: −13.9
[α]D (CHCl$_3$, c=1, 24° C.): −27°
IR(CHCl$_3$) cm$^{-1}$: 1599, 1555, 1345

Example 6
Synthesis of (+)-2-methoxycarbonylamino-2'-diphenylphosphino-1,1'-binaphthyl: the Formula (1-2b)
1.20 gram (2.65 mmol) of (−)-2-amino-2'-diphenylphosphino-1,1'-binaphthyl (1-1a) was dissolved in 53 ml of methylene chloride, followed by the addition of 0.26 ml (3.18 mmol) of pyridine and 0.23 ml (2.91 mmol) of methyl chloroformate under 0° C. The reaction mixture was stirred at room temperature for 21 hours. To the reaction solution, 40 ml of saturated aqueous solution of ammonium chloride was added and extracted with 100 ml of methylene chloride. The extract was washed with 80 ml of brine, and then dried over anhydrous sodium sulfate. The solvent was evaporated under a reduced pressure. The residue was purified using a silica gel column chromatography (eluent: 1:4 mixture of ethyl acetate and hexane) to obtain 1.25 gram of the titled compound.

mp: 92.1° C.
$^1$H-NMR (CDCl$_3$) δ: 8.39(bs, 1H), 8.0–7.8(m, 4H), 7.6–7.4(m, 2H), 7.4–6.9(m, 14H), 6.81(d, J=8.6 Hz, 1H), 5.94(bs, 1H), 3.45(s, 3H)
$^{31}$P-NMR (CDCl$_3$): δ: −13.1
[α]D (CHCl$_3$, c=1, 24° C.): +46°
IR(CHCl$_3$) cm$^{-1}$: 1736, 1599, 1506

Example 7
Synthesis of (+)-2-acetylamino-2'-diphenylphosphino-1,1'-binaphthyl: the Formula (1-2a)
1.15 gram (2.54 mmol) of (−)-2-amino-2'-diphenylphosphino-1,1'-binaphthyl (the formula (1-1a)) was dissolved in 51 ml of methylene chloride, followed by the addition of 0.25 ml (3.04 mmol) of pyridine and 0.20 ml (2.78 mmol) of acetyl chloride under 0° C. The reaction mixture was stirred at room temperature for 3 hours. To the reaction solution, 30 ml of saturated aqueous solution of ammonium chloride was added and extracted with 100 ml of methylene chloride. The extract was washed with 70 ml of brine, and then dried over anhydrous sodium sulfate. The solvent was evaporated under a reduced pressure. The residue was purified using a silica gel column chromatography (eluent: 1:3 mixture of ethyl acetate and hexane) to obtain 1.11 gram of the titled compound.

mp: 104.8° C.
$^1$H-NMR (CDCl$_3$) δ: 8.47(d, J=9.1 Hz, 1H), 8.1–7.8(m, 4H), 7.6–7.4(m, 2H), 7.4–7.0(m, 14H), 6.89(d, J=8.4 Hz, 1H), 6.26(bs, 1H), 1.43(bs, 3H)
$^{31}$P-NMR (CDCl$_3$): δ: −13.7
[α]D (CHCl$_3$, c=1, 24° C.): +17°
IR(CHCl$_3$) cm$^{-1}$: 1687,1598,1499

Example 8
Synthesis of (−)-2-benzoylamino-2'-diphenylphosphino-1,1'-binaphthyl the Formula (1-2c)
1.00 gram (2.21 mmol) of (−)-2-amino-2'-diphenylphosphino-1,1'-binaphthyl (the formula (1-1a)) was dissolved in 44 ml of methylene chloride, followed by the addition of 0.21 ml (2.65 mmol) of pyridine and 0.28 ml (2.43 mmol) of benzoyl chloride under 0° C. The reaction mixture was stirred at room temperature for 5 hours. To the reaction solution, 30 ml of saturated aqueous solution of ammonium chloride was added and extracted with 100 ml of methylene chloride. The extract was washed with 70 ml of brine, and then dried over anhydrous sodium sulfate. The solvent was evaporated under a reduced pressure. The residue was purified using a silica gel column chromatography (eluent: 1:6 mixture of ethyl acetate and hexane) to obtain 1.16 gram of the titled compound.

mp: 94.8° C.

$^1$H-NMR (CDCl$_3$) δ: 8.68(d, J=9.0 Hz, 1H), 8.06(d, J=9.0 Hz, 1H), 7.92(d, J=8.5 Hz, 1H), 7.9–7.8(m, 2H), 7.6–b 7.4(m, 2H ), 7.4–6.9(m, 21H)

$^{31}$P-NMR (CDCl$_3$): δ: −13.1

[α]D (CHCl$_3$, c=1, 24° C.): −20°

1R(CHCl$_3$) cm$^{-1}$: 1673, 1597, 1503, 1428, 1286

Example 9

Synthesis of (−)-2-acetylamino-2'-diphenylphosphinyl-1,1'-binaphthyl (the Formula (1-2a-1)

141 mg (0.30 mmol) of (−)-2-amino-2'-diphenylphosphinyl-1,1'-binaphthyl (the formula (1-1a-1)) was dissolved in 6 ml of methylene chloride, followed by the addition of 29 μl (0.36 mmol) of pyridine and 24 μl (0.33 mmol) of acetyl chloride under 0° C. The reaction mixture was stirred at room temperature for 1 hour. To the reaction solution, 10 ml of saturated aqueous solution of ammonium chloride was added and extracted with 50 ml of methylene chloride. The extract was washed with 20 ml of brine, and then dried over anhydrous sodium sulfate. The solvent was evaporated under a reduced pressure. The residue was purified using a silica gel column chromatography (eluent: 1:4 mixture of ethyl acetate and hexane) to obtain 155 mg of the titled compound.

mp: 95.4° C.

$^1$H-NMR (CDCl$_3$) δ: 9.73(s, 1H), 8.0–7.9(m, 4H), 7.8–7.6 (m, 2H), 7.6–7.4(m, 6H), 7.3–7.1(m, 5H), 7.0–6.9(m, 1H), 6.8–6.7(m, 1H), 6.7–6.6(m, 1H), 6.53(d, J=8.3 Hz, 1H), 1.93(s, 3H)

$^{31}$P-NMR (CDCl$_3$): δ: 29.6

[α]D (CHCl$_3$, c=1, 24° C.): −153°

IR(CHCl$_3$) cm$^{-1}$: 1670, 1597, 1504, 1439, 1167

Example 10

Synthesis of (−)-2-ethylamino-2'-diphenylphosphino-1,1'-binaphthyl: the Formula (1-1c)

127 mg (0.25 mmol) of (−)-2-acetylamino-2'-diphenylphosphinyl-1,1'-binaphthyl (the formula (1-2a-1)) was dissolved in 6 ml of tetrahydrofuran under the flow of nitrogen. To the solution, 620 μl (1.24 mmol) of tetrahydrofuran solution (2M) of borane-dimethyl sulfide complex was added at 0° C., followed by the stirring for 18 hours at 88° C. The reaction solution was extracted with 50 ml of ethyl acetate, washed with 10 ml of saturated aqueous solution of ammonium chloride and 10 m of brine, and then dried over anhydrous sodium sulfate. The solvent was evaporated under a reduced pressure. To the residue, 6 ml of diethylamine was added and stirred under room temperature for 3 hours. Diethylamine was evaporated under a reduced pressure and the residue was purified using a silica gel column chromatography (eluent: 1:50 mixture of ethyl acetate and hexane) to obtain 91 mg of the titled compound.

mp: 83.1° C.

$^1$H-NMR (CDCl$_3$) δ: 8.0–7.8(m, 3H), 7.74(d, J=8.5 Hz, 1H), 7.5–7.4(m, 2H), 7.3–6.9(m, 16H), 6.59(d, J=8.5 Hz, 1H), 3.07(m, 2H), 2.9–2.7(m, 1H), 0.78(d, J=7.0 Hz, 3H)

$^{31}$P-NMR (CDCl$_3$): δ: −13.3

[α]D (CHCl$_3$, c=1, 24° C.): −47°

IR(CHCl$_3$) cm$^{-1}$: 1619, 1599, 1514, 1434, 1302, 1153

Example 11

Synthesis of (−)-2-benzoylamino-2'-diphenylphosphinyl-1,1'-binaphthyl: the Formula (1-2c-1)

188 mg (0.40 mmol) of (−)-2-amino-2'-diphenylphosphinyl-1,1'-binaphthyl (the formula (1-1a-1)) was dissolved in 8 ml of methylene chloride, followed by the addition of 39 μl (0.48 mmol) of pyridine and 51 μl (0.44 mmol) of benzoyl chloride under 0° C. The reaction mixture was stirred at room temperature for 1.5 hours. To the reaction solution, 10 ml of saturated aqueous solution of ammonium chloride was, added and extracted with 50 ml of methylene chloride. The extract was washed with 20 ml of brine, and then dried over anhydrous sodium sulfate. The solvent was evaporated under a reduced pressure. The residue was purified using a silica gel column chromatography (eluent: 1:1 mixture of ethyl acetate and hexane) to obtain 228 mg of the titled compound.

mp: 247.3° C.

$^1$H-NMR (CDCl$_3$) δ: 10.62(s, 1H), 8.0–7.8(m, 7H), 7.72 (d, J=8 Hz, 1H), 7.8–7.1(m, 15H), 7.0–6.9(m, 1H), 6.9–6.7 (m, 1H), 6.7–6.6(m, 1H), 6.51(d, J=7.9 Hz, 1H)

$^{31}$P-NMR (CDCl$_3$): δ: :29.9

[α]D (CHCl$_3$, c=1, 24° C.): −98°

IR(CHCl$_3$) cm$^{-1}$: 1653, 1507, 1489, 1292, 1167

Example 12

Synthesis of (−)-2-benzylamino-2'-diphenylphosphino-1,1'-binaphthyl: the Formula (1-1d)

29 mg (0.05 mmol) of (−)-2-benzoylamino-2'-diphenyl phosphinyl-1,1'-binaphthyl (the formula (1-2c-1)) was dissolved in 1.3 ml of tetrahydrofuran under the flow of nitrogen. To the solution, 88 μl (0.18 mmol) of tetrahydrofuran solution (2M) of borane-dimethyl sulfide complex was added at 0° C., followed by the stirring for 18 hours at 88° C. The reaction solution was extracted with 50 ml of ethyl acetate. The exatract was washed with 10 ml of saturated solution of ammonium chloride and 10 ml of brine, and then dried over anhydrous sodium sulfate. The solvent was evaporated under a reduced pressure. To the residue, 1.5 ml of diethylamine was added and stirred under room temperature for 5 hours. Diethylamine was evaporated under a reduced pressure and the residue was purified using a silica gel column chromatography (eluent: 1:20 mixture of ethyl acetate and hexane) to obtain 24 mg of the titled compound.

mp: 70.1° C.

$^1$H-NMR (CDCl$_3$) δ: 7.9–7.8(m, 2H), 7.80(d, J=8.9 Hz, 1H), 7.69(d, J=8.8 Hz, 1H), 7.6–7.4(m, 2H), 7.4–7.0(m, 19H), 7.0–6.9(m, 1H), 6.61(d, J=8.4 Hz, 1H), 4.17(d, J=15.3 Hz, 1H), 3.99(d, J=15.3 Hz, 1H), 3.68(bs, 1H)

$^{31}$P-NMR (CDCl$_3$): δ: −13.1

[α]D (CHCl$_3$, c=1, 24° C.): −34°

IR(CHCl$_3$) cm$^{-1}$: 1599, 1496, 1342

Example 13

Synthesis of (−)-2-methylsulfonylamino-2'-diphenylphosphinyl-1,1'-binaphthyl: the Formula (1-3a-1)

6.62 gram (14.1 mmol) of (−)-2-amino-2'-diphenylphosphinyl-1,1'-binaphthyl (the formula (1-1a-1)) was dissolved in 282 ml of methylene chloride, followed by the addition of 4.7 ml (57.8 mmol) of pyridine and 4.1 ml (53.6 mmol) of methanesulfonyl chloride at 0° C. The reaction solution was stirred at room temperature for 23 hours. To the reaction solution, 200 ml of saturated aqueous solution of ammonium chloride was added and extracted with 200 ml of methylene chloride. The extract was washed with 200 ml of brine and then dried over anhydrous sodium sulfate. The solvent was evaporated under a reduced pressure. The residue was purified using a silica gel column chromatography (eluent: 2:3 mixture of ethyl acetate and hexane) to obtain 6.15 gram of the titled compound.

mp: 281.9° C.

$^1$H-NMR (CDCl$_3$) δ: 9.31(bs, 1H), 8.0–7.9(m, 4H), 7.80 (d, J=8.2 Hz, 1H), 7.71(d, J=8.8 Hz, 1H), 7.6–7.4(m, 6H), 7.3–7.1(m, 4H), 7.01(d, J=8.8 Hz, 1H), 7.0–6.9(m, 1H), 6.8–6.7(m, 1H), 6.7–6.6(m, 2H), 6.58(d, J=8.3 Hz, 1H), 2.26(s, 3H)

$^{31}$P-NMR (CDCl$_3$): δ: 28.8

[α]D (CHCl$_3$, c=1, 24° C.): −71

IR(CHCl$_3$) cm$^{-1}$: 1324, 1151, 1115

Example 14
Synthesis of Citronellol By the Asymmetric Hydrogenation of Geraniol 4.5 mg (0.01 mmol) of (−)-2-amino-2'-diphenylphosphino-1,1'-binaphthyl (the formula (1-1a)), 5.0 mg (0.01 mmol) of bis(1,5-cyclooctadiene) iridium tetrafluoroborate, 154 mg (1.0 mmol) of geraniol and 2 ml of ethylene chloride were charged into an autoclave and stirred at 30° C. for 20 hours in hydrogen atmosphere under a pressure of 4 atm. The solvent of the resultant reaction solution was evaporated under a reduced pressure. The residue was then measured by means of a gas chromatography to confirm the formation of citronelol with a chemical yield of 77 percent. The optical yield of citronellol was 96 percent confirmed by an optically active HPLC column chromatography.

Chemical Yield
Gas chromatography: GC-17A (Shimadzu seisakusho corporation)
Column chromatography: TC-17 0.25 mm×30 m
Temperature of the column:
Inj.: 200° C.
Coln. 100–120° C.: temperature elevation of 1° C./minute
120–170° C.: temperature elevation of 5° C./minute
Det. 200° C.
Optical Yield:
High performance liquid chromatography: PU-980, UV-970 (Nihon bunko corporation)
Column: CHIRALPAK AD (Daicell chemical corporation)
eluent: n-hexane: 2-propanol=98:2
flow rate: 0.5 ml/minute
detection: 210 nm Example 15
Synthesis of Phenylnorbornane Through Asymmetric Carbon-carbon Bond Formation Between Norbornene and Phenyl Trifluoromethanesulfonate 21 mg (0.04 mmol) of (+)-2-methylsulfonylamino-2'-diphenylphosphino-1-1'-binaphthyl (the formula (1-3a)), 4.5 mg (0.02 mmol) of palladium acetate, 282 mg (3 mmol) of norbornene, 452 mg (2 mmol) of phenyl trifluoromethanesulfonate, 588 mg (7 mmol) of sodium hydrogen carbonate and 5 ml of dimethyl sulfoxide were charged into an autoclave and stirred at 65° C. for 15 hours in hydrogen atmosphere under a pressure of 80 atm. The solvent of the resultant reaction solution was evaporated under a reduced pressure. The residue was then measured by means of a gas chromatography to confirm the formation of exo-phenylnorbornane with a yield of 86 percent. The optical yield of phenylnorbornane was 70 percent confirmed by an optically active HPLC column chromatography.

Chemical Yield
Gas chromatography: GC-17A (Shimadzu seisakusho corporation)
Column chromatography: TC-17 0.25 mm×30 m
Temperature of the column:
Inj.: 200° C.
Coln. 50–200° C.: temperature elevation of 4° C./minute
Det. 200° C.
Optical Yield:
High performance liquid chromatography: PU-980, UV-970 (Nihon bunko corporation)
Column: CHIRALCEL OJ (Daicell chemical corporation)
eluent: n-hexane: 2-propanol=95:5
flow rate: 0.5 ml/minute
detection : 254 nm Reference Example 1
Synthesis of (−)-2-amino-2'-diphenylphosphino-1,1'-binaphthyl: the Formula (1-1a)

7.16 gram (15.2 mmol) of (−)-2-amino-2'-diphenylphosphinyl-1,1'-binaphthyl (the formula (1-1a-1) was dissolved in 381 ml of xylene in an autoclave, followed by the addition of 42.5 ml (305.0 mmol) of triethylamine at 0° C. over 20 minutes and 7.70 ml (76.3 mmol) of trichlorosilane over 1 hour. The mixture was stirred at 150° C. for 18 hours in a tightly sealed condition. The reaction mixture was then extracted with 500 ml of ether. The extract was washed with 200 ml of saturated aqueous solution of ammonium chloride and 200 ml of brine, and then dried over anhydrous sodium sulfate. The solvent was evaporated under a reduced pressure. The residue was purified using a silica gel column chromatography (eluent: 1:4 mixture of ethyl acetate and hexane) to obtain 5.60 gram of the titled compound.

mp: 104.7° C.

$^1$H-NMR (CDCl$_3$) δ: 7.87 (d, J=8.3 Hz, 2H), 7.77 (d, J=8.7 Hz, 1H), 7.71 (d, J=7.8 Hz, 1H), 7.5–7.4 (m, 2H), 7.4–7.2(m, 7H), 7.2–7.0(m, 6H), 7.0–6.9(m, 2H), 6.67(d, J=8.8 Hz, 1H), 3.25(bs, 2H)

$^{31}$P-NMR (CDCl$_3$): δ: −13.1

[α]D (CHCl$_3$, c=1, 24° C.): −27°

IR(CHCl$_3$) cm$^{-1}$: 1622, 1514, 1433

Reference Example 2
Synthesis of (+)-2-methylsulfonylamino-2'-diphenylphosphino-1,1'-binaphthyl: the Formula (1-3a)

3.93 gram (7.17 mmol) of (−)-2-methylsulfonylamino-2'-diphenylphosphinyl-1,1'-binaphthyl (the formula (1-3a-1)) was dissolved in 179 ml of xylene in an autoclave, followed by the addition of 20.0 ml (143.4 mmol) of triethylamine at 0° C. over 15 minutes and 3.62 ml (35.8 mmol) of trichlorosilane over 30 minutes. The mixture was stirred at 150° C. for 18 hours in a tightly sealed condition. The reaction mixture was then extracted with 300 ml of ether. The extract was washed with 100 ml of saturated aqueous solution of ammonium chloride and 100 ml of brine, and then dried over anhydrous sodium sulfate. The solvent was evaporated under a reduced pressure. The residue was purified using a silica gel column chromatography (eluent: 1:6 mixture of ethyl acetate and hexane) to obtain 3.35 gram of the titled compound.

mp: 109.4° C.

$^1$H-NMR (CDCl$_3$) δ: 8.1–7.9(m, 4H), 7.83(d, J=8.3 Hz, 1H), 7.6–37.4(m, 2H), 7.4–7.1(m, 11H), 7.0–6.9(m, 3H), 6.66(d, J=8.3 Hz, 1H), 6.01(s, 1H), 2.59(s, 3H)

$^{31}$P-NMR (CDCl$_3$): δ: −14.0

[α]D (CHCl$_3$, c=1, 24° C.): +41°

IR(CHCl$_3$) cm$^{-1}$: 1306, 1156

What is claimed is:

1. A method for producing an aminophosphine oxide compound represented by the following formula(1)

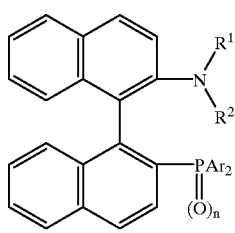
(1)

wherein each Ar represents an aryl group which may be substituted with a halogen atom, a lower alkyl group having 1 to 4 carbon atoms or an alkoxy group, with both Ar's being the same or different from each other; n represents 1; one of $R^1$ and $R^2$ represents a hydrogen atom and the other represents —$COR^3$, wherein $R^3$ represents a lower alkoxy group having 1 to 4 carbon atoms; the method comprising the steps of:

effecting alkaline hydrogen peroxide on 2-cyano-2'-diarylphosphinyl-1,1'-binaphthyl represented by the following formula (4)

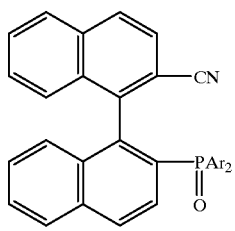
(4)

wherein Ar is the same as above in dimethyl sulfoxide to provide an amidophosphine oxide represented by the following formula (5)

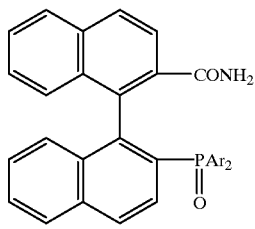
(5)

wherein Ar is the same as above, and reacting said amidophosphine oxide represented by the formula (5), wherein Ar is the same as above, with a metal alkoxide and bromine in an alcohol to provide said aminophosphine oxide compound represented by the formula (1) wherein each Ar represents an aryl group which may be substituted with a halogen atom, a lower alkyl group having 1 to 4 carbon atoms or an alkoxy group, with both Ar's being the same or different from each other; n represents 1; one of $R^1$ and $R^2$ represents a hydrogen atom and the other represents —$COR^3$ (wherein $R^3$ represents a lower alkoxy group having 1 to 4 carbon atoms).

2. A method for producing a 2-amino-2'-diarylphosphinyl-1,1'-binaphthyl represented following formula (1)

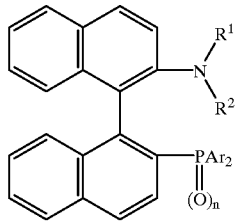
(1)

wherein each Ar represents an aryl group which may be substituted with a halogen atom, a lower alkyl group having 1 to 4 carbon atoms or an alkoxy group, with both Ar's being the same or different from each other; n represents 1; $R^1$ and $l^2$ represent hydrogen atoms by effecting a strong alkaline reagent on an aminophosphine oxide represented by the following formula (1)

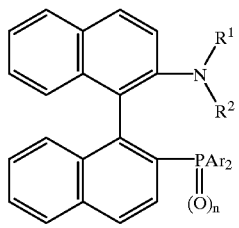
(1)

wherein Ar is the same as above; n represents 1; and
one of $R^1$ and $R^2$ represents a hydrogen atom and the other represents —$COR^3$ wherein $R^3$ represents a lower alkoxy group having 1 to 4 carbon atoms in an alcohol.

3. A method for producing an aminophosphine compound or an aminophosphine oxide compound represented by the following formula (1)

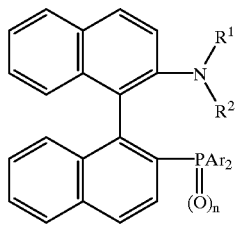
(1)

wherein each Ar represents an aryl group which may be substituted with a halogen atom, a lower alkyl group having 1 to 4 carbon atoms or an alkoxy group, with both Ar's being the same or different from each other;
$R^1$ and $R^2$ represent hydrogen atoms; and
n represents 0 or 1 with a halide represented by the following formula (6)

RX  (6)

wherein X represents Cl or Br; and
R represents —$COR^3$ wherein $R^3$ represents a cycloalkyl group having 5 to 7 carbon atoms, a lower alkyl group having 1 to 6 carbon atoms which may be substituted with a halogen atom, a lower alkoxy group or a phenyl group, a substituted or unsubstituted phenyl group, or a lower alkoxy group having 1 to 6 carbon atoms which may be substituted with a cycloalkyl group having 5 to 7 carbon atoms, a halogen atom, a lower alkoxy group or phenyl group or —$SO_2R^4$ wherein $R^4$ represents a cycloalkyl group having 5 to 7 carbon atoms, an alkyl group having 1 to 6 carbon atoms which may be substituted with a halogen atom, a lower alkoxy group or phenyl group, or substituted or unsubstituted phenyl group in the presence of a base in an organic solvent.

4. A method for producing an aminophosphine compound represented by the following formula (1-0):

formula (1-0):

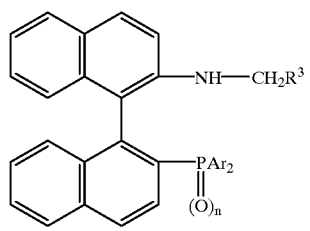

(1-0)

wherein each Ar represents an aryl group which may be substituted with a halogen atom, a lower alkyl group having 1 to 4 carbon atoms or an alkoxy group with both Ar's being the same or different from each other;

n represents 0;

$R^3$ represents a cycloalkyl group having 5 to 7 carbon atoms, a lower alkyl group having 1 to 6 carbon atom which may be substituted with a halogen atom, a lower alkoxy group or phenyl group, or substituted or unsubstituted phenyl group; the method comprising the steps of:

dissolving an aminophosphine compound or an aminophosphine oxide compound represented by the following formula (1)

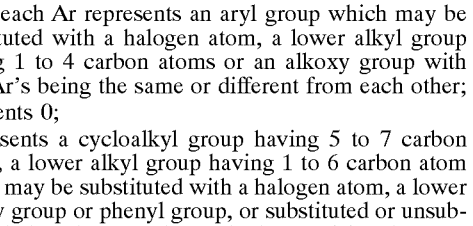

(1)

wherein each Ar represents an aryl group which may be substituted with a halogen atom, a lower alkyl group having 1 to 4 carbon atoms or an alkoxy group with both Ar's being the same or different from each other;

n represents 0 or 1; and one of $R^1$ and $R^2$ represents a hydrogen atom and the other represents —$COR^3$ wherein $R^3$ represents a cycloalkyl group having 5 to 7 carbon atoms, a lower alkyl group having 1 to 6 carbon atoms which may be substituted with a halogen atom, a lower alkoxy group or phenyl group, or a substituted or unsubstituted phenyl group into an organic solvent to obtain a solution;

adding a borane-dimethyl sulfide complex to said solution to react them with each other to obtain a reaction solution;

subjecting said reaction mixture to evaporation to obtain residue;

adding a tertially amine to said residue to react them with each other; and evaporating said tertially amine.

5. A method for producing an aminophosphine compound represented by the following formula (1)

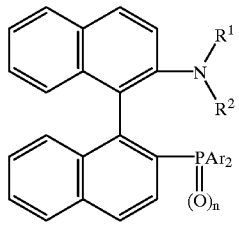

(1)

wherein each Ar represents an aryl group which may be substituted with a halogen atom, a lower alkyl group having 1 to 4 carbon atoms or an alkoxy group with both Ar's being the same or different from each other;

n represents 0; and one of $R^1$ and $R^2$ represents a hydrogen atom and the other represents a methyl group; the method comprising the steps of:

dissolving an aminophosphine compound or an aminophosphine oxide compound represented by the following formula (1)

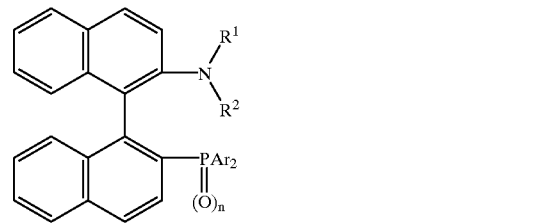

(1)

wherein each Ar is the same as above;

n represents 0 or 1; and one of $R^1$ and $R^2$ represents a hydrogen atom and the other represents —$COR^3$ wherein $R^3$ represents a lower alkoxy group into an organic solvent to obtain a solution;

adding a borane-simethylsulfide complex to said solution to react them with each other to obtain reaction solution;

subjecting said reaction solution to evaporation to provide residue;

adding a tertially amine to said residue to react them with each other; and evaporating said tertially amine.

6. An amidophosphine oxide compound represented by the following formula (5):

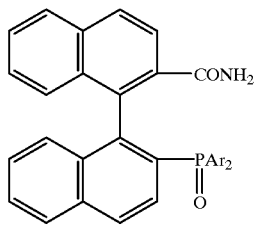

(5)

wherein each Ar represents an aryl group which may be substituted with a halogen atom, a lower alkyl group having 1 to 4 carbon atoms or an alkoxy group.

* * * * *